United States Patent
Keyser et al.

(10) Patent No.: US 12,042,501 B2
(45) Date of Patent: Jul. 23, 2024

(54) METAL PROTOPORPHYRIN FOR TREATMENT OF BK VIRUS

(71) Applicant: Renibus Therapeutics, Inc., Southlake, TX (US)

(72) Inventors: Donald Jeffrey Keyser, Southlake, TX (US); Alvaro F. Guillem, Lantana, TX (US); Bhupinder Singh, Phoenix, AZ (US); Stacey Ruiz, Lantana, TX (US)

(73) Assignee: Renibus Therapeutics, Inc., Southlake, TX (US)

( * ) Notice: Subject to any disclaimer, the term of this patent is extended or adjusted under 35 U.S.C. 154(b) by 27 days.

(21) Appl. No.: 17/860,872

(22) Filed: Jul. 8, 2022

(65) Prior Publication Data

US 2023/0023467 A1    Jan. 26, 2023

Related U.S. Application Data

(60) Provisional application No. 63/220,625, filed on Jul. 12, 2021.

(51) Int. Cl.
| | |
|---|---|
| *A61K 31/555* | (2006.01) |
| *A61K 47/18* | (2017.01) |
| *A61K 47/26* | (2006.01) |
| *A61P 31/12* | (2006.01) |

(52) U.S. Cl.
CPC .......... *A61K 31/555* (2013.01); *A61K 47/18* (2013.01); *A61K 47/26* (2013.01); *A61P 31/12* (2018.01)

(58) Field of Classification Search
None
See application file for complete search history.

(56) References Cited

U.S. PATENT DOCUMENTS

| | | | |
|---|---|---|---|
| 5,756,492 | A | 5/1998 | Buelow et al. |
| 6,066,333 | A | 5/2000 | Willis et al. |
| 9,844,563 | B2 | 12/2017 | Zager et al. |
| 10,639,321 | B2 | 5/2020 | Zager et al. |
| 2006/0166360 | A1 | 7/2006 | Berthiaume et al. |
| 2010/0086519 | A1 | 4/2010 | Bonkovsky et al. |
| 2012/0301866 | A1 | 11/2012 | Martin et al. |
| 2016/0106817 | A1 | 4/2016 | Moss |

OTHER PUBLICATIONS

Ruiz et al., "RBT-9 Antiviral Activity Against BK Virus," Nov. 4, 2021, https://www.asn-online.org/education/kidneyweek/2021/program-abstract.aspx?controlId=3604905>, 2 pages.
Search Report received in International Application No. PCT/US2022/036566 dated Oct. 17, 2022, 2 pages.
Written Opinion received in International Application No. PCT/US2022/036566 dated Oct. 17, 2022, 7 pages.
Assuncao-Miranda et al., "Inactivation of Dengue and Yellow Fever viruses by heme, cobalt-protoporphyrin IX and tin-protoporphyrin IX," Journal of Applied Microbiology, Journal of Applied Microbiology ISSN, Dec. 22, 2015, 15 pages.
Chen, et al., "Preservation Solutions for Kidney Transplantation: History, Advances and Mechanisms," Cell Transplantation 2019, vol. 28, Aug. 5, 2019, 18 pages.
Guo et al., "Alkylated Porphyrins Have Broad Antiviral Activity against Hepadnaviruses, Flaviviruses, Filoviruses, and Arenaviruses," Antimicrobial Agents and Chemotherapy, Feb. 2011, p. 478-486, vol. 55, No. 2, 9 pages.
Hartline, et al., "A standardized approach to the evaluation of antivirals against DNA viruses: Orthopox-, adeno-, and herpesviruses," Antiviral Research 159 (2018), Sep. 28, 2018, 9 pages.
Hou, et al., "Zinc Mesoporphyrin Induces Rapid Proteasomal Degradation of Hepatitis C Nonstructural 5A Protein in Human Hepatoma Cells," Gastroenterology, May 2010, 22 pages.
Leung, et al., "Quantification of polyoma BK viruria in hemorrhagic cystitis complicating bone marrow transplantation," The American Society of Hematology, Sep. 15, 2001, vol. 98, No. 6, 8 pages.
Lu et al., "Broad-spectrum antivirals of protoporphyrins inhibit the entry of highly pathogeni emerging viruses," Bioorganic Chemistry 107, Dec. 27, 2020, 11 pages.
Neris, et al., "Co-protoporphyrin IX and Sn-protoporphyrin IX inactivate Zika, Chikungunya and other arboviruses by targeting the viral envelope," Scientific Reports, Jun. 28, 2018, 13 pages.
Prichard, et al., "Activity and Mechanism of Action of N-Methanocarbathmidine against Herpesvirus and Orthopoxvirus Infections," Antimicrobial Agents and Chemotherapy, Apr. 2006, vol. 50, No. 4, 6 pages.
Staudinger, et al., "Inhibition of Human Immunodeficiency Virus-1 Reverse Transcriptase by Heme and Synthetic Heme Analogs," Proceedings of the Association of American Physicians, Oct. 4, 1995, 8 pages.
Vzorov, et al., "Inactivation of Human Immunodeficiency Virus Type 1 by Porphyrins," Antimicrobial Agents and Chemotherapy, Dec. 2002, vol. 46, No. 12, 9 pages.
Wen, et al., "Synergistic Effect of Zanamivir-Porphyrin Conjugates on Inhibition of Neuraminidase and Inactivation of Influenza Virus," Journal of Medicinal Chemistry, J. Med. Chem. Apr. 23, 2009, 8 pages.

*Primary Examiner* — Noble E Jarrell
(74) *Attorney, Agent, or Firm* — Jeff B. Vockrodt; Culhane PLLC

(57) ABSTRACT

The inactivation of BK virus in patients diagnosed with BK virus, those receiving a kidney that is infected or suspected of being infected by BK virus, or in the transplanted kidney before, during, and/or after transplant surgery is described.

5 Claims, 1 Drawing Sheet

METAL PROTOPORPHYRIN FOR TREATMENT OF BK VIRUS

BACKGROUND OF THE INVENTION

Polyomaviruses are non-enveloped double-stranded DNA viruses with circular genomes of around 5000 base pairs. The genome is packaged in a viral capsid with a diameter of about 40-50 nanometers. BK virus, a member of the polyomavirus family, is a significant risk factor for nephropathy and subsequent allograft loss in patients undergoing kidney transplantation. There are currently no approved treatments for BK virus-induced nephropathy.

Cobalt and tin protoporphyrin have been shown to exhibit broad antiviral activity against enveloped viruses in vitro, but exhibited no activity against the non-enveloped polio virus. See Neris et al., "Co-protoporphyrin IX and Sn-protoporphyrin IX inactivate Zika, Chikungunya and other arboviruses by targeting the viral envelope," Scientific Reports, 8:9805 (2018), DOI:10.1038/s41598-018-27855-7. The Neris paper concluded that the "[i]nefficiency of porphyrins in inactivating a non-enveloped virus further supports the idea that they target the viral envelope."

Other studies have shown activity of metal protoporphyrin against enveloped viruses. Wen W H et al, 2009 J Med Chem. ("Data show additive effect with protoporphyrin conjugated to Zanamivir; antiviral activity could be due to the inhibition of viral neuraminidase and the physical inactivation of the virus through the singlet oxygen reactivity of the protoporphyrin."); Lu et al, 2021 Bioorg Chem. ("Protoporphyrins show broad activity against a panel of enveloped pathogenic viruses, including Lassa virus (LASV), Machupo virus (MACV), SARS-CoV-2, and various subtypes of influenza A strains. IC50 values range from $0.91\pm0.25$ μM to $1.88\pm0.34$ μM"; "In influenza A/Puerto Rico/8/24 (H1N1), protoporphyrin IX inhibits the infection in the early stage of virus entry through biophysically interacting with the hydrophobic lipids of enveloped virions, thereby inhibiting the entry of enveloped viruses into host cells"). Staudinger R et al, 1996 Proc Assoc Am Physicians ("Binds to HIV-1 reverse transcriptase, preventing cDNA synthesis of HIV-1; partly dependent on protoporphyrin structure, as mesoporphyrins had no effect."). Vzorov A N et al, 2002 Antimicrob Agents Chemother. ("MOA assessed with other protoporphyrins, which were shown to Inhibit binding of the HIV-1 gp120 to CD4 and inhibit the ability of Env proteins to include cell fusion to its receptors on target cells."); Guo H et al, 2011 Antimicrob Agents Chemother. ("Alkylated porphyrins used (including hemin); result in disruption and dissociation of HBV envelope proteins from the enveloped particles without degradation of the envelope polypeptides"); Huo W et al, 2010 Gastroenterology ("Antiviral activity assessed with ZnPP; downregulates NS5A protein by enhancing its polyubiquitination and proteasome-dependent catabolism.")' Assuncao-Miranda I et al, 2016 J Appl Microbiol (showing activity against Yellow Fever and Zika Viruses).

There remains a need to find an effective agent for inactivation of the BK virus that is compatible with kidney treatment, and transplant operations.

SUMMARY OF THE INVENTION

In one aspect, the invention involves a method of treating a patient having been diagnosed with BK virus, comprising administering an amount of metal protoporphyrin effective to reduce or eliminate the effects of the BK virus. The metal protoporphyrin may be tin protoporphyrin (SnPP). The patient may have undergone kidney transplant. The metal protoporphyrin may administered at a dose rate ranging from 0.06 to 1.125 mg/kg/day. The dose may range from 5 to 90 mg, with a preferred dose of 90 mg.

In another aspect, the invention involves a method of treating a patient undergoing a kidney transplant surgery comprising before the kidney transplant surgery administering an amount of a first metal protoporphyrin and iron source, and after the transplant surgery administering an amount of a second metal protoporphyrin effective to reduce or eliminate the effects of a BK virus.

In another aspect, the invention involves a kidney storage solution comprising a metal protoporphyrin. The kidney storage solution may also comprise at least one impermeant, and sodium ($Na^+$) and potassium ($K^+$) electrolytes. The impermeant may be glucose, lactobionate, mannitol, raffinose, or combinations thereof. The kidney storage solution may also comprise one or more colloids, additional electrolytes, antioxidants, nutrients, additives, or combinations thereof. The colloid may be hydroxymethyl starch or PEG-35, or combinations thereof. The additional electrolyte may include one or more of calcium ($Ca^{2+}$), chlorine ($Cl^-$), sulphate ($SO_4^{2-}$), phosphate ($PO_4^{3-}$), bicarbonate ($HCO_3^-$), citrate, or combinations thereof. The antioxidant may include allopurinol or glutathione, or combinations thereof. The nutrient may be tryptophan, adenosine, adenine, glutamic acid, histidine, ketoglutarate, or combinations thereof. The additive may include insulin, penicillin, dexamethasone, or combinations thereof. The kidney storage solution preferably has a an osmolarity ranging from 300-500 mOsm/L, and a pH ranging from 7.0 to 7.5.

DETAILED DESCRIPTION OF THE INVENTION

Figure 1:
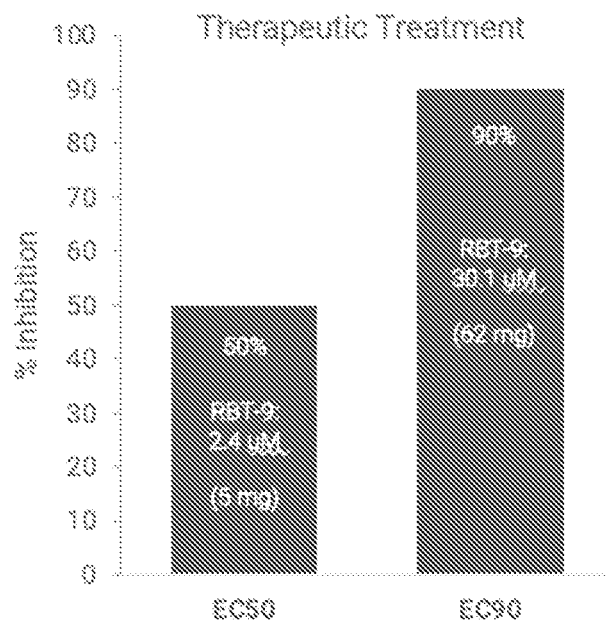
FIG. 1 shows data that demonstrate in vitro effectiveness of SnPP against BK viral infection for therapeutic treatment.
Figure 2:
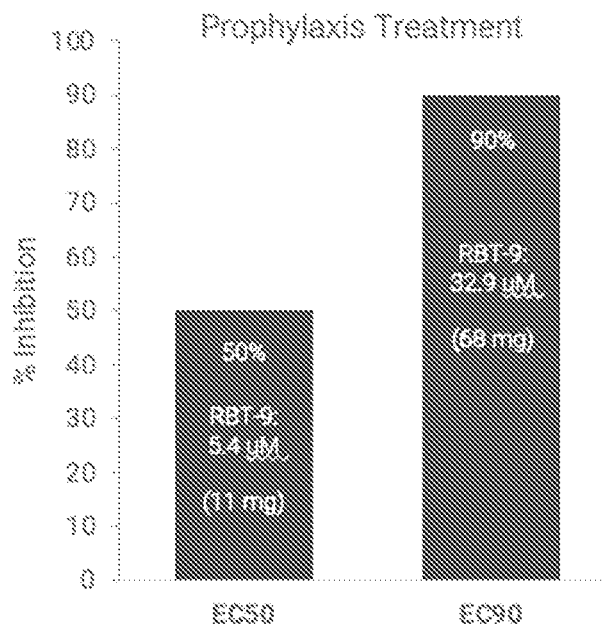
FIG. 2 shows data that demonstrate in vitro effectiveness of SnPP against BK viral infection for prophylaxis treatment.

The present invention relates to the present inventors' discovery that metal protoporphyrins, particularly stannous protoporphyrin (SnPP), have shown an unexpected ability to inactivate a particular polyomavirus, the BK virus. These data demonstrate that SnPP may be used in connection with treatment of BK virus infection in patients diagnosed with the virus, as well as uses of SnPP in connection with kidney transplantation.

Stannous protoporphyrin (SnPP) is known to be protective against acute kidney injury (AKI) in animals when given prior to insult. See U.S. Pat. No. 9,844,563 to Zager et al., entitled "Compositions, kits, and methods to induce acquired cytoresistance using stress protein inducers," granted on Dec. 19, 2017. The present inventors have conducted a Phase I study of SnPP and iron sucrose that demonstrates it is well tolerated.

Although the literature suggested metal protoporphyrins had broad antiviral activity, it was thought based on negative results with the polio virus that metal protoporphyrin activity was limited to enveloped viruses. The inventors unexpectedly discovered that SnPP has broad inactivating activity against certain non-enveloped viruses, including the BK virus, and moderate inactivating activity against the JC virus. This activity was not found with respect to Adenovirus (Adv) and Human Papilloma Virus (HPV).

The present inventors used assays to determine the antiviral activity against various pathogens, including particularly the BK virus. Two conditions were investigated: 1) standard qPCR-based antiviral assay—treatment with SnPP at the time of infection and 2) viral neutralization—pre-incubation of SnPP with BK virus for 1 hour prior to infection. SnPP was tested at concentrations up to 100 μM. Human foreskin fibroblast (HFF) cells were used as the host cell. Viral activity was assessed by real time qPCR and cellular viability was determined by CellTiter-Glo.

Antiviral Materials and Methods

Cell culture. Human foreskin fibroblast (HFF) cells prepared from human foreskin tissue were obtained from the University of Alabama at Birmingham tissue procurement facility with approval from its IRB. The tissue was incubated at 4° C. for 4 h in Clinical Medium consisting of minimum essential media (MEM) with Earl's salts supplemented with 10% fetal bovine serum (FBS) (Hyclone, Inc. Logan UT), L-glutamine, fungizone, and vancomycin. Tissue is then placed in phosphate buffered saline (PBS), minced, rinsed to remove the red blood cells, and resuspended in trypsin/EDTA solution.

The tissue suspension is incubated at 37° C. and gently agitated to disperse the cells, which are collected by centrifugation. Cells are resuspended in 4 ml Clinical Medium and placed in a 25 cm² flask and incubated at 37° C. in a humidified $CO_2$ incubator for 24 h. The media is then replaced with fresh Clinical Medium and the cell growth is monitored daily until a confluent monolayer has formed. The HFF cells are then expanded through serial passages in standard growth medium of MEM with Earl's salts supplemented with 10% FBS, L-glutamine, penicillin, and gentamycin. The cells are passaged routinely and used for assays at or below passage 10. See Hartline et al., "A standardized approach to the evaluation of antivirals against DNA viruses: Orthopox-, adeno-, and herpesviruses," Antiviral Res. 2018, November; 159:104-112. doi: 10.1016/j.antiviral.2018.09.015. Epub 2018 Oct. 1. PMID: 30287226; Prichard et al., "Activity and mechanism of action of N-methanocarbathymidine against herpesvirus and orthopoxvirus infections," Antimicrob Agents Chemother, 2006; 50(4):1336-41. PubMed PMID: 16569849; PubMed Central PMCID: PMC1426929. COS 7 fibroblast cells were obtained from ATCC and maintained in standard growth medium of MEM with Earl's salts supplemented with 10% FBS, L-glutamine, penicillin, and gentamycin.

Assays for BK virus and JC virus. Primary assays for BKV and JCV were performed by methods reported previously. See Keith et al., supra. For BKV, compound dilutions were prepared in plates containing cells, subsequently infected and incubated for 7d. Total DNA was prepared and genome copy number was quantified by real time PCR using the primers 5'-AGT GGA TGG GCA GCC TAT GTA-3', 5'-TCA TAT CTG GGT CCC CTG GA-3' and probe 5'-6-FAM AGG TAG AAG AGG TTA GGG TGT TTG ATG GCA CAG TAMRA-3'. See Leung et al., "Quantification of polyoma BK viruria in hemorrhagic cystitis complicating bone marrow transplantation," Blood. 2001; 98(6):1971-8, PubMed PMID: 11535537. Plasmid pMP526 serves as the DNA standard for quantification purposes. Compounds that were positive in this assay were confirmed in a similar assay in 96-well plates according to established laboratory protocols with the compounds added 1 h post infection to identify compounds that inhibit early stages of replication including adsorption and penetration. Genome copy number was determined by methods described above.

Primary evaluation of compounds against JC virus were also performed by methods similar to those for BK virus primary assays but were done in COS7 cells and utilized the 1-4 strain of JCV in COS7 cells. Viral DNA was quantified using primers 5'-CTG GTC ATG TGG ATG CTG TCA-3' and 5'-GCC AGC AGG CTG TTG ATA CTG-3' and probe 5'-6-FAM-CCC TTT GTT TGG CTG CT-TAMRA-3 together with the plasmid pMP508 to provide a standard curve for absolute quantification. Secondary assays against JCV were also performed in COS7 cells by methods similar to those for BK virus to identify compounds that inhibited adsorption or penetration of the virus.

$EC_{50}$—compound concentration that reduces viral replication by 50%

$EC_{90}$—compound concentration that reduces viral replication by 90%

$CC_{50}$—compound concentration that reduces cell viability by 50%

$SI_{50}$—$CC_{50}/EC_{50}$ $SI_{90}$—$CC_{50}/EC_{90}$

| SnPP treatment of BK Virus (20-bk-007) Quantitative polymerase chain reaction (DNA)/CellTiter-Glo (Toxicity) | | | | | | |
|---|---|---|---|---|---|---|
| Virus Screened | BK Virus | | | | | |
| Virus Strain | Gardner | | | | | |
| Cell Line | HFF | | | | | |
| Vehicle | DMSO | | | | | |
| Agent | Concentration Range | $EC_{50}$ | $EC_{90}$ | $CC_{50}$ | $SI_{50}$ | $SI_{90}$ |
| Cidofovir | 0.048-150 μM | 6.28 | 117.05 | >150.00 | >24 | >1 |
| SnPP | 0.048-150 μM | 8.08 | 26.62 | 62.30 | 8 | 2 |

| SnPP treatment of BK Virus (21-bk2-001) Quantitative polymerase chain reaction (DNA)/CellTiter-Glo (Toxicity) | | | | | | |
|---|---|---|---|---|---|---|
| Virus Screened | BK Virus | | | | | |
| Virus Strain | Gardner | | | | | |
| Cell Line | HFF | | | | | |
| Vehicle | DMSO | | | | | |
| Agent | Concentration Range | $EC_{50}$ | $EC_{90}$ | $CC_{50}$ | $SI_{50}$ | $SI_{90}$ |
| Cidofovir | 0.048-150 μM | 0.72 | 10.74 | >100.00 | >139 | >9 |
| SnPP | 0.048-150 μM | 2.40 | 30.09 | 95.75 | 40 | 3 |

| SnPP treatment of BK Virus (21-bk2-003) Quantitative polymerase chain reaction (DNA)/CellTiter-Glo (Toxicity) | | | | | | |
|---|---|---|---|---|---|---|
| Virus Screened | BK Virus | | | | | |
| Virus Strain | Gardner | | | | | |
| Cell Line | HFF | | | | | |
| Vehicle | DMSO | | | | | |
| Agent | Concentration Range | $EC_{50}$ | $EC_{90}$ | $CC_{50}$ | $SI_{50}$ | $SI_{90}$ |
| Cidofovir | 0.001-100 μM | 0.13 | 17.90 | >100.00 | >769 | >6 |
| SnPP | 0.001-100 μM | 8.6 | 81.8 | 82.7 | 10 | 1 |

| SnPP treatment of BK Virus (21-bk2-004) Quantitative polymerase chain reaction (DNA)/CellTiter-Glo (Toxicity) | | | | | | |
|---|---|---|---|---|---|---|
| Virus Screened | BK Virus | | | | | |
| Virus Strain | Gardner | | | | | |
| Cell Line | HFF | | | | | |
| Vehicle | DMSO | | | | | |
| Agent | Concentration Range | $EC_{50}$ | $EC_{90}$ | $CC_{50}$ | $SI_{50}$ | $SI_{90}$ |
| Cidofovir | 0.001-100 μM | >100 | >100 | >100.00 | 1 | 1 |
| SnPP | 0.001-100 μM | 5.4 | 32.9 | 82.7 | 15 | 3 |

SnPP exhibited moderate antiviral activity against BK virus under both treatment conditions. The 50% effective concentration ($EC_{50}$) averaged 5.5 μM in 2 independently run standard qPCR assays and 5.4 μM in the neutralization assay. The $EC_{50}$ of SnPP in these assays is 11 times lower than the highest dose of SnPP tested in Phase 1 studies and considered to be well tolerated. The 50% cytotoxic concentration ($CC_{50}$) in the in vitro studies averaged 89.2 μM, indicating SnPP did not adversely affect host cell viability at concentrations 16.5 times higher than its effective concentration.

Given the antiviral activity of SnPP against BK virus in vitro and the safety profile of SnPP in Phase 1 human studies, a clinical study assessing the efficacy of SnPP is warranted in patients who are at risk of developing BK virus-induced nephropathy.

The present inventors sought to determine whether the SnPP activity would be uniform for several polyomaviruses, including Adv, HPV, BK and JC. In general, an $SI_{50}$ of greater than 10 is required to be considered potentially effective. The most significant activity was observed with BK virus, followed by JC virus with moderate activity. Minimal to no activity was observed with the Adv and HPV. The following data summarize the ability of SnPP to inactivate several viruses:

These data demonstrate that metal protoporphyrin, including SnPP, can inactivate the BK virus. In one aspect, SnPP can be used as a stand-alone therapy to treat patients that have been diagnosed with a BK viral infection. In this regard, the patient may be treated after receiving a positive PCR test indicating the presence of BK virus. The treatment may comprise administering an effective amount of metal protoporphyrin, such as SnPP, to the patient for the inactivation of BK virus. The treatment may comprise an injection of SnPP at a dose ranging from 5-120 mg, more preferably 50-100 mg, and most preferably between 80-95 mg. For example, a dose of 90 mg. 4. The metal protoporphyrin may be administered at a dose rate ranging from 0.06 to 1.125 mg/kg/day. The dosing may be continued daily, weekly, or monthly until a PCR test indicates the inactivation of BK virus in the patient.

In another example, a patient expected to receive a kidney transplant may receive a dose of metal protoporphyrin, such as SnPP, before, during, and/or after receiving the organ. In this case, the patient may receive the dose of metal protoporphyrin when the transplanted organ is known to be infected with BK virus. Otherwise, a patient may be treated prophylactically when it is unknown whether the organ to be transplanted is infected with the BK virus.

| Virus | Type | Activity | Assay Order | $EC_{50}$ | $EC_{90}$ | $CC_{50}$ | $SI_{50}$ |
|---|---|---|---|---|---|---|---|
| AdV | Non-enveloped | NONE | Primary | >30.00 | >30.00 | 30.92 | <1 |
| HPV (HPV11) | Non-enveloped | MINIMAL | Primary | 23.45 | >30.00 | 121.84 | 5 |
| CMV | Enveloped | NONE | Primary | >6.00 | >6.00 | 20.51 | <3 |
| BK | Non-enveloped | MODERATE | Primary | 8.08 | 26.62 | 62.3 | 8 |
| BK | Non-enveloped | HIGH | Secondary | 2.4 | 30.09 | 95.75 | 40 |
| BK | Non-enveloped | MODERATE | Primary (Standard) | 8.6 | 81.8 | 82.7 | 10 |
| BK | Non-enveloped | MODERATE | Secondary (Neutralization [Pre-incubation of Virus with RBT-9]) | 5.4 | 32.9 | 82.7 | 15 |
| JC | Non-enveloped | MODERATE | Primary | 5.38 | >30.00 | 99.83 | 19 |
| JC | Non-enveloped | MODERATE | Primary (Standard) | 9.93 | 63.1 | 72.1 | 7 |
| JC | Non-enveloped | MINIMAL | Secondary (Neutralization [Pre-incubation of Virus with RBT-9]) | 18.9 | >20.00 | 72.1 | 4 |

In one case, the present method may be combined with known methods for treating a patient in advance of surgery to protect against acute kidney injury. In those cases, a patient may be administered a combination of SnPP and iron sucrose before the surgery. In the case where a patient is diagnosed with BK viral infection, the patient may then receive treatment with metal protoporphyrin (without a supplemental iron source) after the surgery.

In one aspect, organs that are removed for transplantation are stored in a transport liquid or cold storage liquid that includes a metal protoporphyrin to inactivate any BK virus that may be present within the organ to be transplanted. Several cold storage liquids are known in the art, including Euro-Collins Solution (EC); hyperosmolar solution (HOC) solution also known as Marshall's solution; University of Wisconsin (UW) solution containing lactobionate and raffinose; histidine-tryptophan-ketoglutarate (HTK) solution; and Celsior.

In one embodiment, the transport liquid comprises at least one impermeant, electrolytes comprising at least sodium ($Na^+$) and potassium ($K^+$), and the metal protoporphyrin. The metal protoporphyrin may be selected from a cobalt, zinc or tin protoporphyrin. Preferably the metal porphyrin is tin protoporphyrin (SnPP). The impermeant may be selected from one or more of glucose, lactobionate, mannitol, raffinose, or combinations thereof. Optional additional components include colloids, additional electrolytes, antioxidants, nutrients, additives, or combinations thereof. Colloids may include, for example, hydroxymethyl starch or PEG-35, or combinations thereof. Additional electrolytes may include calcium ($Ca^{2+}$), chlorine ($Cl^-$), sulphate ($SO_4^{2-}$), phosphate ($PO_4^{3-}$), bicarbonate ($HCO_3^-$), citrate, or combinations thereof. Antioxidants may include allopurinol or glutathione, or combinations thereof. Nutrients may include tryptophan, adenosine, adenine, glutamic acid, histidine, ketoglutarate, or combinations thereof. Additives may include insulin, penicillin, dexamethasone, or combinations thereof. The osmolarity of the transport liquid may preferably range from 300-500 mOsm/L, and the pH may preferably range from 7.0 to 7.5. Cold storage solutions are described in Chen et al., "Preservation Solutions for Kidney Transplantation: History, Advances and Mechanisms," Cell Transplant. 28(12): 1472-1489 (2019), which is incorporated by reference herein in its entirety.

The transport liquid comprising a metal protoporphyrin may be provided within a kit that includes a sterile sealable pouch containing transport liquid. During the transport of the organ, the organ can be subject to inactivation of any BK virus that may be present by exposure to the transport liquid. In one aspect, the organ may be subject to the transport liquid after having been determined to contain the BK virus. In this case, the patient receiving the organ may be administered metal protoporphyrin before, during or after the transplant surgery.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A method of treating a patient having been diagnosed with BK virus, comprising administering an amount of metal protoporphyrin effective to reduce or eliminate the effects of the BK virus.

2. The method of claim 1, wherein the metal protoporphyrin is tin protoporphyrin (SnPP).

3. The method of claim 1, wherein the patient has undergone kidney transplant.

4. The method of claim 1, wherein the metal protoporphyrin is administered at a dose rate ranging from 0.06 to 1.125 mg/kg/day.

5. The method of claim 1, wherein the metal protoporphyrin is administered at a daily dose ranging from 5 to 90 mg.

* * * * *